United States Patent
Vartiainen (12)

(10) Patent No.: US 6,410,819 B1
(45) Date of Patent: Jun. 25, 2002

(54) METHOD OF PRODUCING AN ABSORBENT STRUCTURE HAVING IMPROVED STRENGTH PROPERTIES

(75) Inventor: Kent Vartiainen, Lerum (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

(21) Appl. No.: 09/297,884

(22) PCT Filed: Nov. 12, 1997

(86) PCT No.: PCT/SE97/01890

§ 371 (c)(1),
(2), (4) Date: May 11, 1999

(87) PCT Pub. No.: WO98/20821

PCT Pub. Date: May 22, 1998

(30) Foreign Application Priority Data

Nov. 12, 1996 (SE) .................................. 9604123

(51) Int. Cl.⁷ ................................................. A61F 13/15
(52) U.S. Cl. .................... 604/367; 264/121; 264/122; 604/358
(58) Field of Search ................................ 264/121, 122; 604/358, 367

(56) References Cited

U.S. PATENT DOCUMENTS

| 4,551,142 A | 11/1985 | Kopolow |
| 4,590,114 A | 5/1986 | Holtman |
| 5,013,309 A | 5/1991 | Baigas, Jr. et al. |
| 5,516,569 A | 5/1996 | Veith et al. |

FOREIGN PATENT DOCUMENTS

| EP | 0 122 042 A3 | 10/1984 |

*Primary Examiner*—Mary Lynn Theisen
(74) *Attorney, Agent, or Firm*—Burns, Doane, Swecker & Mathis, L.L.P.

(57) ABSTRACT

A method of producing an absorbent structure that includes hydrophilic fibres and particles of superabsorbent material, comprising forming an air-laid structure from fibres and superabsorbent particles. At least a part of the air-laid structure is moistened to a moisture content in the moistened region of at least 15% calculated on the total weight of the structure within the moistened region, whereafter the structure is dried to a moisture content of at most 12%. The moisture treatment improves the tensile strength of the absorbent structure. Liquid dispersion in the structure is also improved.

18 Claims, 2 Drawing Sheets

METHOD OF PRODUCING AN ABSORBENT STRUCTURE HAVING IMPROVED STRENGTH PROPERTIES

FIELD OF INVENTION

The present invention relates to a method of producing an air-laid absorbent structure that includes hydrophilic fibres and particles of superabsorbent material. Such absorbent structures are used in sanitary articles, such as diapers, incontinence guards, sanitary napkins and like articles.

DESCRIPTION OF THE BACKGROUND ART

An absorbent structure in a sanitary article of the aforesaid kind intended for one-time use only is typically comprised of one or more layers of hydrophilic fibres, normally cellulose fluff pulp. The structure will also often include so-called superabsorbents, which are polymers that can absorb many times their own weight in water or body liquid. Such an absorbent structure is flexible and comfortable to wear, and also has a high absorption capacity.

One drawback of these known absorbent structures is their relatively low strength properties, particularly tensile strength. which can sometimes cause problems in the various steps of manufacturing the sanitary article in question and also during the use of said article. Various attempts have been made to enhance the strength and the structural coherency of such absorbent structures. among other things by mixing-in thermoplastic synthetic fibres with subsequent heating of the absorbent structure, c.f. for instance U.S. Pat. No. 4,590,114. The thermoplastic fibres are therewith melted and contribute towards a more coherent structure that has improved strength properties. The drawback with this solution is the relatively high price of the thermoplastic fibres and the negative influence that this so-called thermobonding has on the absorption properties.

A method of producing a wet-laid absorbent structure of relatively high tensile strength is disclosed in U.S. Pat. No. 4,551,142. for instance. This method involves providing an aqueous dispersion of cellulose fibres and superabsorbent particles, formation of this dispersion into a wet-laid sheet which is then dewatered, dried and compressed to the desired density. The procedure and equipment required in this process are completely different to those normally applied in the air-laying method, in which cellulose pulp in bale or sheet form is dry-shredded to form so-called fluff pulp and air-laid to form a pulp mat together with superabsorbent particles.

U.S. Pat. No. 5,516,569 discloses that an absorbent composite containing 40 to 85% superabsorbent particles is wetted to a moisture content of between 15 to 30% in order to bind the superabsorbent particles in the composite.

OBJECTS AND MOST IMPORTANT FEATURES OF THE INVENTION

The object of the present invention is to provide a method of producing an absorbent structure formed in accordance with an air-laying method and having considerably improved strength properties. This object is achieved in accordance with the invention by moistening the air-laid structure to a moisture content of at least 15%, preferably at least 20%. and more preferably at least 35%, calculated on the total weight of the structure, and thereafter drying the structure to a moisture content of at most 12%, preferably at most 10%.

When the absorbent structure is moistened or wetted to a high moisture content, water may be pressed from the structure prior to drying the same.

The structure is preferably moistened with distilled water or de-ionized water.

The inventive method is flexible, by virtue of the fact that it is only necessary to moisten or wet certain parts of the structure in order to obtain better strength. For instance, the structure can be moistened in a suitable moistening pattern, e.g. in a strip pattern or network pattern. In the case of profile structures where different parts of the structure have mutually different weights per unit area, it may be suitable to moisten only those parts that have the lowest weight per unit area and therewith the lowest strength.

DESCRIPTION OF THE INVENTION

Figure 1:
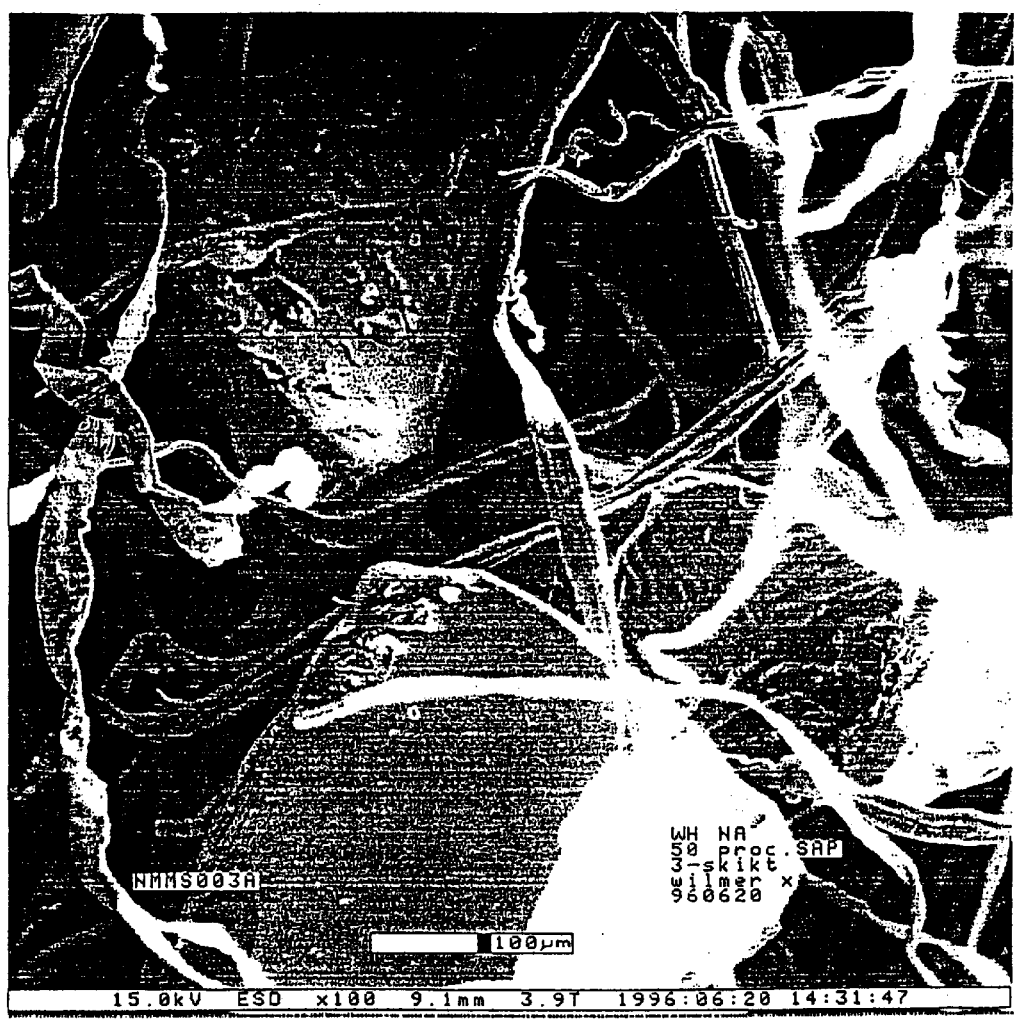
FIG. 1 is an electron microscope photograph of a fluff pulp structure that includes superabsorbent particles.

The absorbent structure is formed by a conventional air-laying method, see, for instance, EP 0 192 042, according to which cellulose pulp is dry-shredded to cellulose fluff pulp and a mixture of this pulp and superabsorbent particles is air-laid to form a web, or is air-laid in moulds on a so-called mat-forming, wheel, for forming the absorbent structure. The superabsorbent particles may alternatively be applied as a layer between pulp layers, instead of being admixed with the pulp fibres. It is also possible to form two or more layers one on top of the other. These layers may contain mutually different percentages of superabsorbent, different types of pulp fibres and/or superabsorbent, so as to impart desired properties to the absorbent structure, such as liquid acquisition, liquid dispersion and liquid storage properties. The construction of such absorbent structures is well known in the art and will not therefore be described in detail here.

The cellulose fibres may be comprised of chemical pulp, mechanical pulp, thermomechanical or chemithermomechanical pulp (CTMP). Fibres of chemically cross-linked cellulose may also be used. Other types of hydrophilic fibres are regenerated cellulose (viscose), polyester and hydrophobic fibres that have been treated with a hydrophilizing agent.

Various different types of superabsorbents may be used. A common feature of these superabsorbents is that they are polymers which are capable of absorbing and binding water or body liquid in quantities corresponding to many times their own weight. Examples of polymers that are used to this end are polyacrylates, alginates, polysaccharides, such as cellulose derivatives, starch derivatives, etc., and copolymers and graft polymers thereof.

The superabsorbent particles will preferably be present in an amount corresponding to at least 3% calculated on the total weight of the structure before moistening, preferably at least 5% and at most 80%, preferably at most 70% and more preferably at most 35% superabsorbent particles.

The air-laid absorbent structure is moistened with water in the moistened region to a moisture content of at least 15%, preferably at least 20% and more preferably at least 35%. calculated on the total weight of the structure. The term moistening as used here also includes wetting the structure with water to the saturation concentration in the wetted regions. The water used will preferably be distilled water or de-ionized water, which has the least possible affect on the absorbency of the superabsorbents subsequent to moistening and drying the structure.

The entire structure may be moistened, or solely parts of said structure. For instance, the structure may be moistened in longitudinally extending or transversely extending strips, in a network pattern or in some other pattern judged to be suitable in context. In the case of absorbent structures that have a profiled appearance, where different parts of the structure have different weights per unit areas it may be suitable to moisten only those parts that have the lowest weight per unit area and are therewith the weakest.

Figure 2:
FIG. 2 is a corresponding photograph of a corresponding structure treated in accordance with the invention.

The structure is thereafter dried in some suitable way to a moisture content of at most 12%, preferably at most 10%, calculated on the total weight of the structure. Part of the liquid may be pressed mechanically from the structure prior to drying said structure. This may be appropriate when an excessive amount Of liquid has been used to moisten the structure. The absorbent structure will preferably remain moist over a time period of at least one minute. This is to enable the superabsorbent particles to absorb liquid and swell. Swelling of the superabsorbent particles results in a certain adhesion between superabsorbent and pulp fibres, and it can be said that the swollen superabsorbents function as a binder in the fibre structure that increases the strength of said structure. As will be evident from FIGS. 1 and 2, the superabsorbent grains do not retain their original particle shape after treatment, but instead "creep" along and between the fibres.

After being dried, the structure can be compressed to the density desired, preferably between 0.06 and 0.3 g/cm$^3$. The tensile strength of the thus produced absorbent structure will be much higher than the tensile strength of a corresponding structure that has not been subjected to moisture treatment.

The absorbent structure can be incorporated as an absorbent body in an absorbent article, such as a diaper, an incontinence guard, a sanitary napkin and like article. The absorbent structure is herewith typically enclosed between a liquid-permeable top sheet, which suitably comprises a nonwoven material or a perforated plastic film, and a liquid-impermeable backing sheet, normally comprised of plastic film, e.g. polyethylene film. In certain cases, a liquid-acquisition material in the form of porous wadding or nonwoven material may be arranged between the top sheet material and absorbent body. The absorbent article may also be provided with elastic devices that shape and adapt the article to the wearer's body.

With the intention of discovering how such moisture treatment affects the properties of the absorbent structure, tests were carried out on the following pulp/superabsorbent mixtures:

A) STORA CTMP+7% superabsorbent IM 7100 from Hoechst.
B) Korsnäs Vigorfluff A (chemical pulp)+30% superabsorbent IM 7100.
C) Weyerhaeuser NB 416 (chemical pulp)+30% superabsorbent IM 7100.
D) Chemical pulp (200 g/m$^2$)+60% superabsorbent IM 7100.

Sample bodies measuring 50×100 mm and containing a mixture of pulp fibres and superabsorbent particles were punched-out. The samples were compressed to a bulk value of 6 cm$^3$/g (density 0.17 g/cm$^3$) and thereafter conditioned for 24 h. The tensile strength of the samples was measured in an Instron apparatus. The sample bodies were then wetted with de-ionized water, substantially to saturation, and thereafter dried at 50° C. over 10–14 hours. The samples were conditioned and the bulk adjusted to 6 cm$^3$/g (density 0.17 g/cm$^3$). The tensile strength of the samples was measured in the same way as that described above. The results obtained are given in the following Tables.

TABLE 1

Tensile strength of samples before and after treatment.

| Sample | A before | A after | B before | B after | C before | C after | D before | D after |
|---|---|---|---|---|---|---|---|---|
| Tensile strength (N/50 mm) | 0.88 | 8.32 | 5.75 | 16.98 | 5.76 | 16.14 | 1.22 | 9.38 |

The measurement values constitute the mean value of seven measuring processes.

It will be seen that the tensile strength was increased manifold as a result of the treatment.

When the chemical pulp has a very high content of superabsorbent particles as in Example D, the tensile strength is low. The tensile strength increases with the treatment. However, the strength is still low in comparison with the strength of the other treated chemical pulps containing only 30% superabsorbent.

With the intention of discovering how the absorbent properties were affected by the treatment, measurements were carried out with respect to absorbency and dispersion distance. The measurements were carried out in accordance with the following methods:

The samples were placed in the test equipment with one part horizontal and one part inclined at 60°, and allowed to absorb liquid in accordance with the self-suction principle from an "infinite" source. After a given period of time (the absorption time), the extent to which the liquid had dispersed was determined (the dispersion distance). The amount of liquid that had been absorbed (the absorption) was also measured with the aid of scales.

The sample was then placed in liquid and allowed to absorb freely, whereafter the sample was placed on a grating and loaded with a weight of 7.0 kg for a period of 5 min. The sample was weighed to give the free absorption under load. The measurement values thus obtained can then be used to calculate a measurement of the sample utilization potential (utilization degree) in accordance with:

$$\frac{\text{Abs.} - \text{Sample Weight}}{\text{Free abs.} - \text{Sample weight}} \times 100\,(\%)$$

The results are given in Table 2 below.

TABLE 2

Absorption properties before and after treatment.

| Sample | A before | A after | B before | B after | C before | C after | D before | D after |
|---|---|---|---|---|---|---|---|---|
| Sample weight (g) | 16 | 15 | 37 | 37 | 37 | 37 | 24.5 | 24.4 |
| Abs. (g) | 125 | 127 | 426 | 432 | 378 | 419 | 397 | 407 |
| Utilize degree (%) | 38 | 45 | 53 | 60 | 47 | 60 | 57 | 56 |
| Free abs. after loading (g) | 302 | 259 | 775 | 690 | 764 | 675 | 681 | 714 |
| Abs. time (min) | 60 | 60 | 120 | 120 | 120 | 120 | 150 | 150 |
| Disp distance (cm) | 25.5 | 34 | 28.5 | 34 | 26.5 | 34.5 | 25.7 | 26.3 |

The measurement values constitute the mean measurement of three measuring processes.

It will be seen from these measurements that the dispersion distance increased after treatment, which also gives a higher degree of utilization. On the other hand, a slightly lower free absorption was obtained after loading the sample, which can be assumed to be because the ability of the superabsorbent to take-up liquid has been impaired after treatment. This is compensated for, however, by the improved dispersion distance, and hence absorption was roughly the same before and after treatment.

When the pulp has a high content of superabsorbent, above about 50%, the dispersion distance will not increase as much as for the pulps having a lower content of superabsorbent. Neither will the utilization potential increase as much. This is demonstrated by Example D where both the dispersion distance and the utilization potential remain essentially unchanged by the treatment.

Thus, a superabsorbent content below 60% is preferred, especially a content below 50%, a content below 40 or 35% being most preferred.

What is claimed is:

1. A method of producing an absorbent structure that includes hydrophilic fibres and particles of superabsorbent material, comprising forming an air-laid structure of fibres and superabsorbent particles, moistening at least part of said air-laid structure to a moisture content in the moistened region of at least 15%, calculated on the total weight of the structure within the moistened region, and thereafter drying the structure to a moisture content of at most 12%, the structure containing 3–35% superabsorbent particles, calculated on the total weight of the structure before moistening.

2. A method according to claim 1, where the absorbent structure contains at least 5% superabsorbent particles, calculated on the total weight of the structure before moistening.

3. A method according to claim 1, comprising moistening to a moisture content in the moistened region of at least 20%, calculated on the total weight of the structure within the moistened region.

4. A method according to claim 3, comprising moistening to a moisture content in the moistened region of at least 35%, calculated on the total weight of the structure within the moistened region.

5. A method according to claim 1, comprising drying the structure to a moisture content of at most 10%.

6. A method according to claim 1, comprising moistening the structure with distilled or de-ionized water.

7. A method according to claim 1, comprising pressing water from the moistened structure, prior to drying said structure.

8. A method according to claim 1, comprising moistening only certain parts of the structure.

9. A method according to claim 8, comprising moistening the structure in such a pattern or within such parts of the structure that the total tensile strength of said structure is enhanced.

10. An absorbent article, including an absorbent structure obtained by the method according to claim 1.

11. A method according to claim 2, comprising moistening to a moisture content in the moistened region of at least 20%, calculated on the total weight of the structure within the moistened region.

12. A method according to claim 2, comprising drying the structure to a moisture content of at most 10%.

13. A method according to claim 2, comprising moistening the structure with distilled or de-ionized water.

14. A method according to claim 2, comprising pressing water from the moistened structure, prior to drying said structure.

15. A method according to claim 2, comprising moistening only certain parts of the structure.

16. An absorbent article, including an absorbent structure obtained by the method according to claim 2.

17. An absorbent article according to claim 10, wherein the absorbent article is a diaper, incontinence guard, or a sanitary napkin.

18. An absorbent article according to claim 16, wherein the absorbent article is a diaper, incontinence guard, or a sanitary napkin.

* * * * *